United States Patent [19]

Glen

[11] 4,191,775

[45] Mar. 4, 1980

[54] AMIDE DERIVATIVES

[75] Inventor: Alasdair T. Glen, Macclesfield, England

[73] Assignee: Imperial Chemical Industries Limited, London, England

[21] Appl. No.: 964,726

[22] Filed: Nov. 29, 1978

[30] Foreign Application Priority Data

Dec. 15, 1977 [GB] United Kingdom ............... 52223/77

[51] Int. Cl.$^2$ ................. A61K 31/165; A61K 31/275; C07C 103/127; C07C 121/78
[52] U.S. Cl. .............................. 424/304; 260/465 D; 260/562 B; 424/324
[58] Field of Search ....................... 260/465 D, 562 B; 424/304, 324

[56] References Cited

U.S. PATENT DOCUMENTS

| | | | |
|---|---|---|---|
| 3,794,683 | 2/1974 | Gassner et al. | 260/562 B |
| 3,875,229 | 4/1975 | Gold | 260/562 B |

*Primary Examiner*—Dolph H. Torrence
*Attorney, Agent, or Firm*—Cushman, Darby & Cushman

[57] ABSTRACT

The disclosure relates to novel 3,4-disubstituted-branched-chain-fluorinated-acylanilides, processes for their manufacture and pharmaceutical compositions containing them. The compounds possess antiandrogenic activity. Representative of the compounds disclosed is 4-nitro-3-trifluoromethyl-(2-hydroxy-2-trifluoromethylpropionyl)anilide.

9 Claims, No Drawings

AMIDE DERIVATIVES

This invention relates to new amide derivatives and more particularly it relates to novel acylanilides which possess antiandrogenic properties.

According to the invention there is provided an acylanilide of the formula:

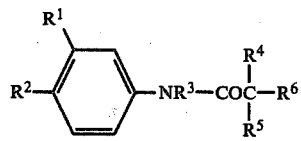

wherein $R^1$ is cyano, nitro, trifluoromethyl, chloro, bromo, iodo, hydrogen or alkyl of up to 4 carbon atoms;
wherein $R^2$ is cyano, nitro, trifluoromethyl, chloro, bromo or iodo;
wherein $R^3$ is hydrogen or alkyl of up to 4 carbon atoms;
wherein $R^4$ is alkyl of up to 4 carbon atoms;
wherein $R^5$ is trifluoromethyl, difluoromethyl or monofluoromethyl;
and wherein $R^6$ is hydrogen, hydroxy, halogen, alkyl or alkoxy each of up to 4 carbon atoms, arylalkoxy of up to 10 carbon atoms or acyloxy of up to 15 carbon atoms.

A suitable value for $R^1$, $R^3$, $R^4$ or $R^6$ when it is alkyl is, for example, methyl or ethyl.

A suitable value for $R^6$ when it is halogen is fluoro, chloro, bromo or iodo.

A suitable value for $R^6$ when it is alkoxy is, for example, methoxy or ethoxy.

A suitable value for $R^6$ when it is arylalkoxy is, for example, benzyloxy.

A suitable value for $R^6$ when it is acyloxy is, for example, alkanoyloxy of up to 15 carbon atoms, for example acetoxy, propionyloxy or decanoyloxy.

It will be observed that the acylanilide derivative of the invention possesses an asymmetric carbon atoms, namely the carbon atom of the —$CR^4R^5R^6$ group, and it can therefore exist in racemic and optically-active forms. It is to be understood that this invention encompasses the racemic form of the acylanilide derivative and any optically-active form which possesses antiandrogenic activity, it being a matter of common general knowledge how a racemic compound may be resolved into its optically-active forms and how any antiandrogenic activity present in any of these forms may be determined.

A preferred acylanilide of the invention has the formula stated above wherein $R^1$ and $R^2$, which may be the same or different, each is cyano, nitro, trifluoromethyl, chloro or bromo, $R^3$ is hydrogen, $R^4$ is methyl, $R^5$ has the meaning stated above and $R^6$ is hydroxy.

Specific acylanilides of the invention are hereinafter described in the Examples. Particularly active compounds are 3,4-dicyano-(2-hydroxy-2-trifluoromethylpropionyl)anilide, 3-chloro-4-nitro-(2-hydroxy-2-trifluoromethylpropionyl)anilide, 3,4-dichloro-(2-hydroxy-2-trifluoromethylpropionyl)anilide, 4-nitro-3-trifluoromethyl-(2-hydroxy-2-trifluoromethylpropionyl)anilide and 4-cyano-3-trifluoromethyl-(2-hydroxy-2-trifluoromethylpropionyl)anilide, and of these the last two are preferred.

The acylanilides of the invention may be manufactured by any chemical process known to be suitable for the manufacture of chemically-analogous compounds.

A preferred process for the manufacture of an acylanilide of the invention comprises the reaction of an amine of the formula:

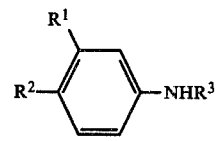

wherein $R^1$, $R^2$ and $R^3$ have the meanings stated above, with an acid of the formula:
$$HOCOCR^4R^5R^6$$

wherein $R^4$, $R^5$ and $R^6$ have the meanings stated above, or with a reactive derivative of said acid.

A suitable reactive derivative of an acid is, for example, an acid anhydride, or an acyl halide, for example an acyl chloride, or a lower alkyl ester of said acid, for example the methyl or ethyl ester. The reactive derivative may be prepared in situ, for example by reacting the acid with thionyl chloride in a dipolar aprotic solvent such as N,N-dimethyacetamide, hexamethylphosphoric triamide or N-methylpyrrolidinone.

An alternative process for the manufacture of an acylanilide derivative of the invention wherein $R^6$ is hydroxy comprises the Smiles' rearrangement of an amide of the formula:

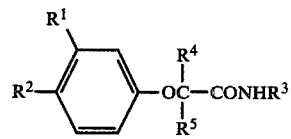

wherein $R^1$, $R^2$, $R^3$, $R^4$ and $R^5$ have the meanings stated above.

The rearrangement may be carried out by treating the amide with a strong base, for example an alkali metal hydride, for example sodium hydride, under anhydrous conditions. The reaction is conveniently carried out at laboratory temperature.

An acylanilide of the invention wherein $R^3$ is alkyl may be prepared by the alkylation of the corresponding acylanilide wherein $R^3$ is hydrogen.

An acylanilide of the invention wherein $R^6$ is acyloxy may be prepared by the acylation of the corresponding acylanilide wherein $R^6$ is hydroxy, and an acylanilide of the invention wherein $R^6$ is hydroxy may be prepared by the hydrolysis of the corresponding acylanilide wherein $R^6$ is acyloxy.

As stated above, an acylanilide of the invention possesses antiandrogenic properties as demonstrated by its ability to decrease the weight of the seminal vesicles and ventral prostate of a castrated male rate when administered concurrently with testosterone propionate. An acylanilide of the invention may therefore be used in the treatment of, for example, malignant or benign prostatic disease or of androgen-dependent disease conditions, such as acne, hirsutism or seborrhoea, in warm-blooded vertebrates including man. It may also be used to improve ovulation in a domestic animal.

A preferred acylanilide of the invention is up to 4 times more active as an antiandrogen than the known, chemically-related antiandrogens flutamide and hydroxyflutamide. At a dose of an acylanilide of the invention which produces antiandrogenic activity in rats no symptons of toxicity are apparent.

The acylanilide of the invention may be administered to a warm-blodded animal in the form of a pharmaceutical or veterinary composition which comprises the acylanilide in association with a pharmaceutically-acceptable diluent or carrier.

The composition may be in a form suitable for oral dosage, as a tablet, capsule, aqueous or oily solution or suspension or emulsion. It may alternatively be in the form of a sterile solution or suspension suitable for parenteral administration, or be in the form of an ointment or lotion for topical administration, or be in the form of a suppository.

The composition may additionally contain one or more drugs selected from anti-oestrogens, for example tamoxifen; progestins, for example medroxyprogesterone acetate; inhibitors of gonadotrophin secretion, for example danazol; cytotoxic agents, for example cyclophosphamide; antibiotics, for example penicillin or oxytetracyclin; and anti-inflammatory agents, for example, especially for topical use, fluocinolone acetonide.

The acylanilide of the invention will normally be administered to a warm-blooded animal at a dose of between 0.1 mg. and 25 mg. per kg. bodyweight.

The invention is illustrated but not limited by the following Examples:

EXAMPLE 1

A mixture of 3,4-dichloroaniline (0.5 g.) and 2-hydroxy-2-trifluoromethylpropionic acid (0.6 g.) is heated at 180° C. for 3 hours and then cooled and shaken with a mixture of ethyl acetate and water. The ethyl acetate layer is separated, washed with dilute aqueous sodium hydroxide solution and then with water, dried over magnesium sulphate and evaporated to dryness. The residue is chromatographed on a silica gel column (200 g.) using a 20% v/v solution of ethyl acetate in chloroform as eluant. The eluant is collected and evaporated to dryness and the residue is crystallised from toluene. There is thus obtained 3,4-dichloro-(2-hydroxy-2-trifluoromethylpropionyl)-anilide, m.p. 125°–127° C.

EXAMPLE 2

Thionyl chloride (0.25 ml.) is added to a stirred solution of 2-hydroxy-2-trifluoromethylpropionic acid (0.5 g.) in hexamethylphosphoric triamide (1 ml.) which is cooled to −10° C., and the mixture is stirred at 10° C. for 1 hours. 3,4-Dicyanoaniline (0.3 g.) is added, and the mixture is stirred for 1 hour at laboratory temperature and then diluted with water. The mixture is extracted with ethyl acetate and the extract is washed with dilute aqueous sodium hydroxide solution and then with water, dried over magnesium sulphate and evaporated to dryness. The residue is dissolved in ethyl acetate and the solution is passed through a short column of silica gel. The eluate is evaporated to dryness and the residue is crystallised from a mixture of ethyl acetate and petroleum ether (b.p. 60°–80° C.). There is thus obtained 3,4-dicyano-(2-hydroxy-2-trifluoromethylpropionyl)anilide, m.p. 153°–155° C.

The process described above is repeated except that the appropriate aniline is used in place of dicyanoaniline. There are thus obtained the compounds shown in the following table:

$$R^2 \underset{R^1}{\underset{|}{\text{—}}} \text{—NHCOC(CH}_3\text{)(CF}_3\text{)—OH}$$

| $R^1$ | $R^2$ | m.p. (°C.) |
|---|---|---|
| chloro | nitro | 125–127 |
| trifluoromethyl | nitro | 129–131 |

EXAMPLE 3

Thionyl chloride (0.8 ml.) is added to a stirred solution of 2-hydroxy-2-monofluoromethylpropionic acid (1.2 g.) in N,N-dimethylacetamide (10 ml.) which is cooled to −20° C., and the mixture is stirred at that temperature for 1 hour. 3,4-Dicyanoaniline (0.5 g.) is added and the mixture is stirred at laboratory temperature for 16 hours and then diluted with water and extracted with ethyl acetate. The extract is washed with water, dried and evaporated to dryness. The residual oil is dissolved in toluene and chromatographed on a magnesium trisilicate (50 g.) column using a 3:1 v/v mixture of toluene and ethyl acetate as eluant. The eluate is evaporated to dryness and the residue is crystallised from toluene. There is thus obtained 3,4-dicyano-(2-hydroxy-2-monofluoromethylpropionyl)anilide, m.p. 176°–178° C.

The process described above or in Example 2 is repeated using the appropriate aniline and the appropriate 2-hydroxy-2-(fluorinated-methyl) propionic acid as starting materials. There are thus obtained the compounds described in the following tables:

$$R^2 \underset{R^1}{\underset{|}{\text{—}}} \text{—NHCOC(CH}_3\text{)(CF}_3\text{)—OH}$$

| $R^1$ | $R^2$ | m.p. (°C.) | solvent used in reaction* | Note |
|---|---|---|---|---|
| H | CN | 159–160 | H | |
| H | CF$_3$ | 141–143 | D | |
| CH$_3$ | CN | 175–177 | D | |
| NO$_2$ | CN | 153–155 | D | |
| NO$_2$ | Cl | 119–121 | D | |
| CN | NO$_2$ | 125–126 | D | |
| CN | Cl | 141–143 | H | |
| CN | Br | 148–150 | H | |
| CN | CN | 128–131 | H | (+)-Isomer† |
| CF$_3$ | NO$_2$ | 123–125 | D | (+)-Isomer† |
| CF$_3$ | NO$_2$ | 123–125 | D | (−)-Isomer† |
| CF$_3$ | CN | 152–154 | H | ** |
| CF$_3$ | Br | 140–141 | H | |

*D indicated N,N-dimethylacetamide (this Example) H indicated hexamethylphosphoric triamide (Example 2)

† The (+)-isomer is obtained by using (+)-2-hydroxy-2-trifluoromethylpropionic acid, and the (−)-isomer by using (−)-2-hydroxy-2trifluoromethyl-propionic acid, as starting material

[Structure: benzene ring with R¹ para, R² meta, and NHCOC(CH₃)(R⁵)OH substituent]

| R¹ | R² | R⁵ | m.p. (°C.) | solvent used in reaction |
|---|---|---|---|---|
| CF₃ | NO₂ | CH₂F | 128–130 | D |
| CF₃ | NO₂ | CHF₂ | 119–121 | D |
| Cl | Cl | CHF₂ | 114–116 | D |
| CF₃ | CN | CHF₂ | 136–138 | D |

EXAMPLE 4

3,4-Dichloroaniline (0.5 g.) is added to a solution of 2-methoxy-2-trifluoromethylpropionyl chloride (1.5 g.) in pyridine (10 ml.) and the mixture is stirred at laboratory temperature for 16 hours, diluted with water and extracted with ethyl acetate. The extract is washed with water, dried and evaporated to dryness and the residue is dissolved in toluene and chromatographed on a magnesium trisilicate (40 g.) column using a 4:1 v/v mixture of toluene and ethyl acetate as eluant. The eluate is evaporated to dryness and the residue is crystallised from aqueous ethanol. There is thus obtained 3,4-dichloro-(2-methoxy-2-trifluoromethylpropionyl)anilide, m.p. 53°14 55° C.

The acid chloride used as starting material may be obtained as follows:

Methyl iodide (1.42 g.) is added to a stirred solution of sodium hydride (0.8 g. of a 60% w/w dispersion in mineral oil) in N,N-dimethylacetamide (10 ml.) and the mixture is stirred at laboratory temperature for 1 hour, diluted with water, acidified with dilute aqueous hydrochloric acid and extracted with ethyl acetate. The extract is dried over magnesium sulphate and evaporated to dryness. The residue is dissolved in a mixture of thionyl chloride (10 ml.) and N,N-dimethylformamide (0.1 ml.) and the mixture is heated under reflux for 2 hours and the excess of thionyl chloride is then removed by evaporation. The residue consists of 2-methoxy-2-trifluoromethylpropionyl chloride and is used without further pruification.

EXAMPLE 5

The process described in Example 4 is repeated except that 2-benzyloxy-2-trifluoromethylpropionyl chloride (prepared in a similar manner to that described in the second part of Example 4 except that benzyl bromide is used in place of methyl iodide) is used as starting material. There is thus obtained 3,4-dichloro-(2-benzyloxy-2-trifluoromethylpropionyl)anilide, m.p. 83°–85° C.

EXAMPLE 6

A mixture of 3,4-dichloroaniline (1.0 g.) and 2-hydroxy-2-trifluoromethylbutyric acid (1.5 g.) is heated at 200° C. for 4 hours, cooled and shaken with a mixture of ethyl acetate and water. The ethyl acetate layer is washed with dilute aqueous hydrochloric acid and then with water, dried and evaporated to dryness. The residue is dissolved in toluene and chromatographed on a magnesium trisilicate (40 g.) column using an 17:3 v/v mixture of toluene and ethyl acetate as eluant.

The eluate is evaporated to dryness and the residue is crystallised from toluene. There is thus obtained 3,4-dichloro-(2-hydroxy-2-trifluoromethyl-butyryl)anilide, m.p. 122°–124° C.

The butyric acid used as starting material may be obtained as follows:

1,1,1,-Trifluorobutan-2-one (14 g.) is added dropwise to a stirred solution of potassium cyanide (8.2 g.) in water (30 ml.) which is maintained at 0° C. 25% V/v aqueous sulphuric acid (50 ml.) is added and the mixture is stirred at laboratory temperature for 16 hours and is then extracted with ether. The extract is washed with water, dried and evaporated to dryness and the residual oil is added dropwise to concentrated sulphuric acid (6 ml.) which is maintained at 70°–75° C. Water (50 ml.) is added and the mixture is heated at 95°–100° C. for 72 hours, cooled and extracted with ether. The ethereal extract is washed with water and then extracted with saturated aqueous sodium bicarbonate solution. The extract is acidified with equeous hydrochloric acid and then extracted with ether. The ethereal extract is washed with water, dried and evaporated to dryness and the residue is crystallised from a mixture of chloroform and petroleum ether (b.p. 60°–80° C.). There is thus obtained 2-hydroxy-2-trifluoromethylbutyric acid, m.p. 95°–100° C.

EXAMPLE 7

A mixture of 3-chloro-4-nitro-(2-hydroxy-2-trifluoromethylpropionyl)anilide (2.0 g.), sodium hydride (0.55 g. of a 60% suspension in mineral oil) and N,N-dimethylformamide (30 ml.) is stirred at laboratory temperature until effervescence ceases. Methyl iodide (22.8 g.) is added and the mixture is stirred at laboratory temperature for 16 hours and then diluted with water and extracted with ethyl acetate. The extract is washed with water, dried and evaporated to dryness and the residue is crystallised from a mixture of toluene and petroleum ether (b.p. 60°–80° C.). There is thus obtained 3-chloro-4-nitro-(2-methoxy-2-trifluoromethylpropionyl)-N-methylanilide, m.p. 72°–74° C.

EXAMPLE 8

A mixture of 3,4-dicyano-(2-hydroxy-2-trifluoromethylpropionyl)anilide (0.5 g.), acetyl chloride (2 ml.) and concentrated aqueous hydrochloric acid (0.1 ml.) is heated at 95°–100° C. for 16 hours, diluted with water and extracted with ethyl acetate. The extract is washed with water, dried and evaporated to dryness and the residue is crystallised twice from a mixture of chloroform and petroleum ether (b.p. 60°–80° C.). There is thus obtained 3,4-dicyano-(2-acetoxy-2-trifluoromethylpropionyl)anilide, m.p. 103°–105° C.

The process described above is repeated except that 4-nitro-3-trifluoromethyl-(2-hydroxy-2-trifluoromethylpropionyl)anilide and decanoyl chloride was used as starting materials. The crude product is purified by chromatography on a silica gel column using toluene as eluant, and the purified product is crystallised from a mixture of ether and petroleum ether (b.p. 60°–80° C.). There is thus obtained 4-nitro-3-trifluoromethyl-(2-decanoyloxy-2-trifluoromethylpropionyl)anilide, m.p. 56°–57° C.

EXAMPLE 9

Concentrated aqueous hydrochloric acid (0.5 ml.) is added to a solution of 4-nitro-3-trifluoromethyl-(2-hydroxy-2-trifluoromethylpropionyl)anilide (1.04 g.) in acetic anhydride (4.5 ml.) and the mixture is heated at 95°–100° C. for 48 hours and then diluted with water and filtered. The solid residue is dried and crystallised from chloroform and there is thus obtained 4-nitro-3-trifluoromethyl-(2-acetoxy-2-trifluoromethylpropionyl)aniline, m.p. 148°–150° C.

EXAMPLE 10

A mixture of 4-nitro-3-trifluoromethyl-(2-hydroxy-2-trifluoromethylpropionyl)anilide (1.0 g.), sodium hydride (0.3 g. of a 60% suspension in mineral oil) and dry N,N-dimethylformamide (10 ml.) is stirred at laboratory temperature until effervescence ceases. n-Propyl iodide (6.8 g.) is added and the mixture is heated at 80° C. for 48 hours, diluted with water and extracted with ethyl acetate. The extract is washed with water, dried and evaporated to dryness and the residue is chromatographed on a magnesium trisilicate (30 g.) column using a 20:1 v/v mixture of toluene and ethyl acetate as eluant. The eluate is evaporated to dryness and the residue is crystallised from a mixture of toluene and petroleum ether (b.p. 60°–80° C.). There is thus obtained 4-nitro-3-trifluoromethyl-(2-n-propoxy-2-trifluoromethylpropionyl)anilide, m.p. 77°–79° C.

EXAMPLE 11

The process described in Example 6 is repeated except that 2-hydroxy-2-trifluoromethylhexanoic acid (prepared from 1,1,1-trifluorohexan-2-one by a similar process to that described in the second part of Example 6) is used as starting material in place of 2-hydroxy-2-trifluoromethylbutyric acid. There is thus obtained 3,4-dichloro(2-hydroxy-2-trifluoromethylhexanoyl)anilide, m.p. 101°–103° C.

What we claim is:

1. An acylanilide of the formula:

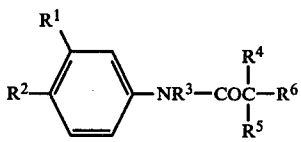

wherein $R^1$ is cyano, nitro, trifluoromethyl, chloro, bromo, iodo, hydrogen or alkyl of up to 4 carbon atoms;

wherein $R^2$ is cyano, nitro, trifluoromethyl, chloro, bromo or iodo;

wherein $R^3$ is hydrogen or alkyl of up to 4 carbon atoms;

wherein $R^4$ is alkyl of up to 4 carbon atoms;

wherein $R^5$ is trifluoromethyl, difluoromethyl or monofluoromethyl;

and wherein $R^6$ is hydrogen, hydroxy, halogen, alkyl or alkoxy each of up to 4 carbon atoms, arylalkoxy of up to 10 carbon atoms or alkanoyloxy of up to 15 carbon atoms.

2. An acylanilide as claimed in claim 1 wherein $R^1$ and $R^2$, which may be the same or different, each is cyano, nitro, trifluoromethyl, chloro or bromo, $R^3$ is hydrogen, methyl or ethyl, $R^4$ is methyl or ethyl, $R^5$ has the meaning stated in claim 1 and $R^6$ is hydrogen, hydroxy, methoxy, ethoxy, benzyloxy, acetoxy, propionyloxy or decanoyloxy.

3. An acylanilide as claimed in claim 1 wherein $R^1$ and $R^2$, which may be the same or different, each is cyano, nitro, trifluoromethyl, chloro or bromo, $R^3$ is hydrogen, $R^4$ is methyl, $R^5$ has the meaning stated in claim 1 and $R^6$ is hydroxy.

4. The compound 3,4-dicyano-(2-hydroxy-2-trifluoromethylpropionyl)anilide, 3-chloro-4-nitro-(2-hydroxy-2-trifluoromethylpropionyl)anilide or 3,4-dichloro-(2-hydroxy-2-trifluoromethylpropionyl)anilide.

5. The compound 4-nitro-3-trifluoromethyl-(2-hydroxy-2-trifluoromethylpropionyl)anilide.

6. The compound 4-cyano-3-trifluoromethyl-(2-hydroxy-2-trifluoromethylpropionyl)anilide.

7. A pharmaceutical or veterinary composition which comprises an acylanilide, claimed in claim 1, in association with a pharmaceutically acceptable diluent or carrier.

8. A composition as claimed in claim 7 which additionally contains one or more drugs selected from antioestrogens, progestins, inhibitors of gonadotrophin secretion, cytotoxic agents, antibiotics and anti-inflammatory agents.

9. A method of producing an antiandrogenic effect in a warm-blooded animal in need of such an effect which comprises administering to said animal an effective amount of an acylanilide claimed in claim 1.